(12) United States Patent
Bompard et al.

(10) Patent No.: US 7,101,181 B2
(45) Date of Patent: Sep. 5, 2006

(54) SYSTEM FOR FIXING A DENTAL IMPLANT

(75) Inventors: Bruno Bompard, Paris (FR); Elisabeth Bompard, Paris (FR); Guy Hure, Paris (FR)

(73) Assignee: Guy Hure, Paris (FR)

( * ) Notice: Subject to any disclaimer, the term of this patent is extended or adjusted under 35 U.S.C. 154(b) by 123 days.

(21) Appl. No.: 10/991,463

(22) Filed: Nov. 19, 2004

(65) Prior Publication Data

US 2005/0069835 A1    Mar. 31, 2005

Related U.S. Application Data

(63) Continuation-in-part of application No. 10/048,941, filed as application No. PCT/FR00/01807 on Jun. 28, 2000, now Pat. No. 6,824,384.

(30) Foreign Application Priority Data

Aug. 6, 1999    (FR)    .................................. 99 10375

(51) Int. Cl.
*A61C 3/00*    (2006.01)

(52) U.S. Cl. ....................................................... 433/75

(58) Field of Classification Search ............ 433/74–76, 433/173–175; 606/96–98
See application file for complete search history.

(56) References Cited

U.S. PATENT DOCUMENTS

| | | | | |
|---|---|---|---|---|
| 3,765,034 A | * | 10/1973 | Johnston .................... 623/22.4 |
| 4,044,466 A | * | 8/1977 | Pasqualini et al. .......... 433/176 |
| 5,108,398 A | * | 4/1992 | McQueen et al. ............ 606/62 |
| 5,176,681 A | * | 1/1993 | Lawes et al. ................. 606/64 |
| 5,334,192 A | * | 8/1994 | Behrens ........................ 606/96 |

* cited by examiner

*Primary Examiner*—Melba N. Bumgarner
(74) *Attorney, Agent, or Firm*—Stites & Harbison PLLC; Douglas E. Jackson

(57) ABSTRACT

A drilling system includes a drilling jig which is used for a dental implant where the dental implant has a bore designed to received a clamp of the drilling jig. The bore enables the drilling jig to be guided for producing one or several lateral holes in the bone and for passing through one or several pins. The dental implant also includes a jig body accurately fixed on a positioning member integral with the dental implant, and an elongated part or socket which slides in the jig body to be urged in contact with the bone. A pin and pin holder cooperate with each other and the jig.

12 Claims, 3 Drawing Sheets

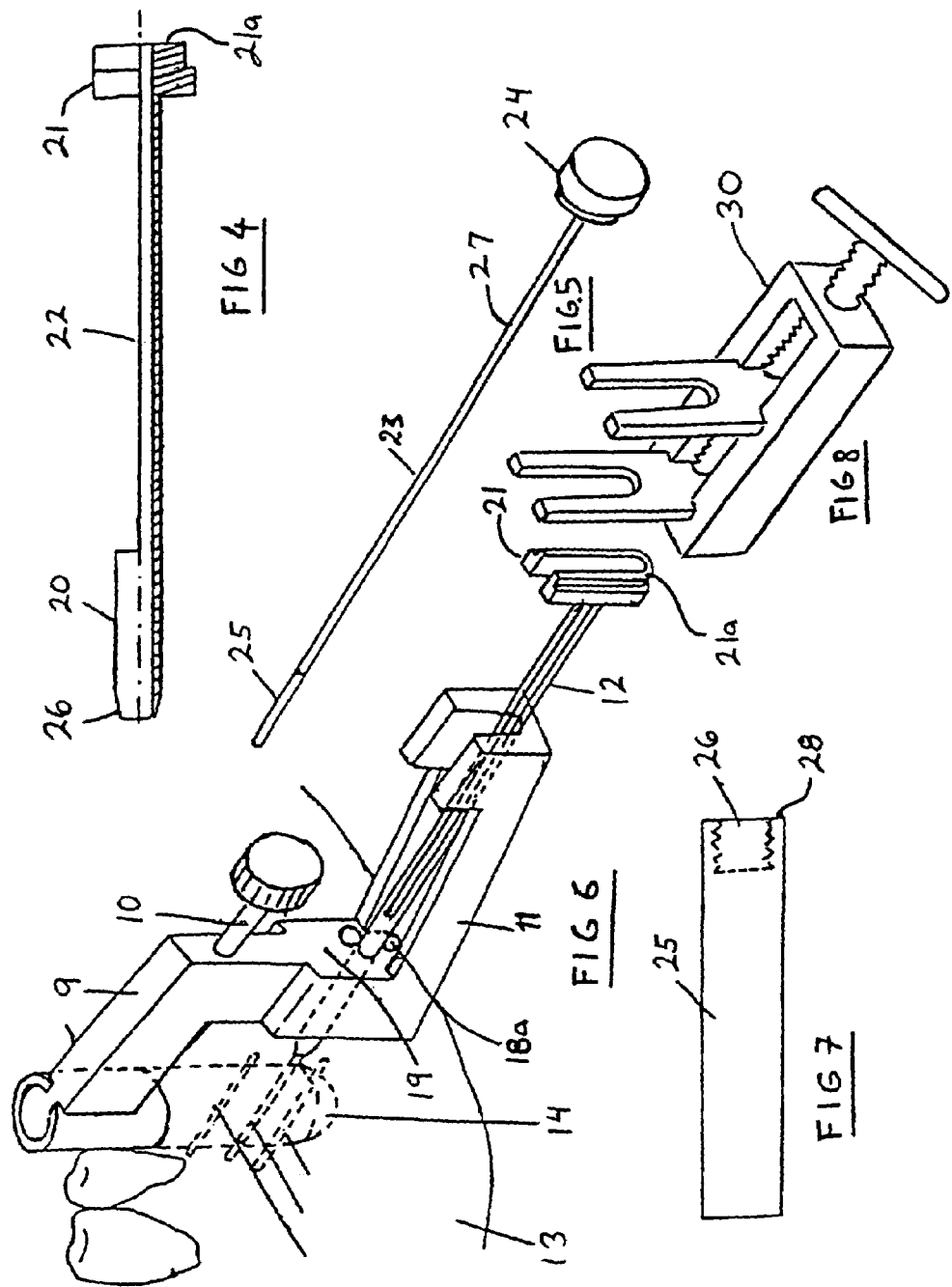

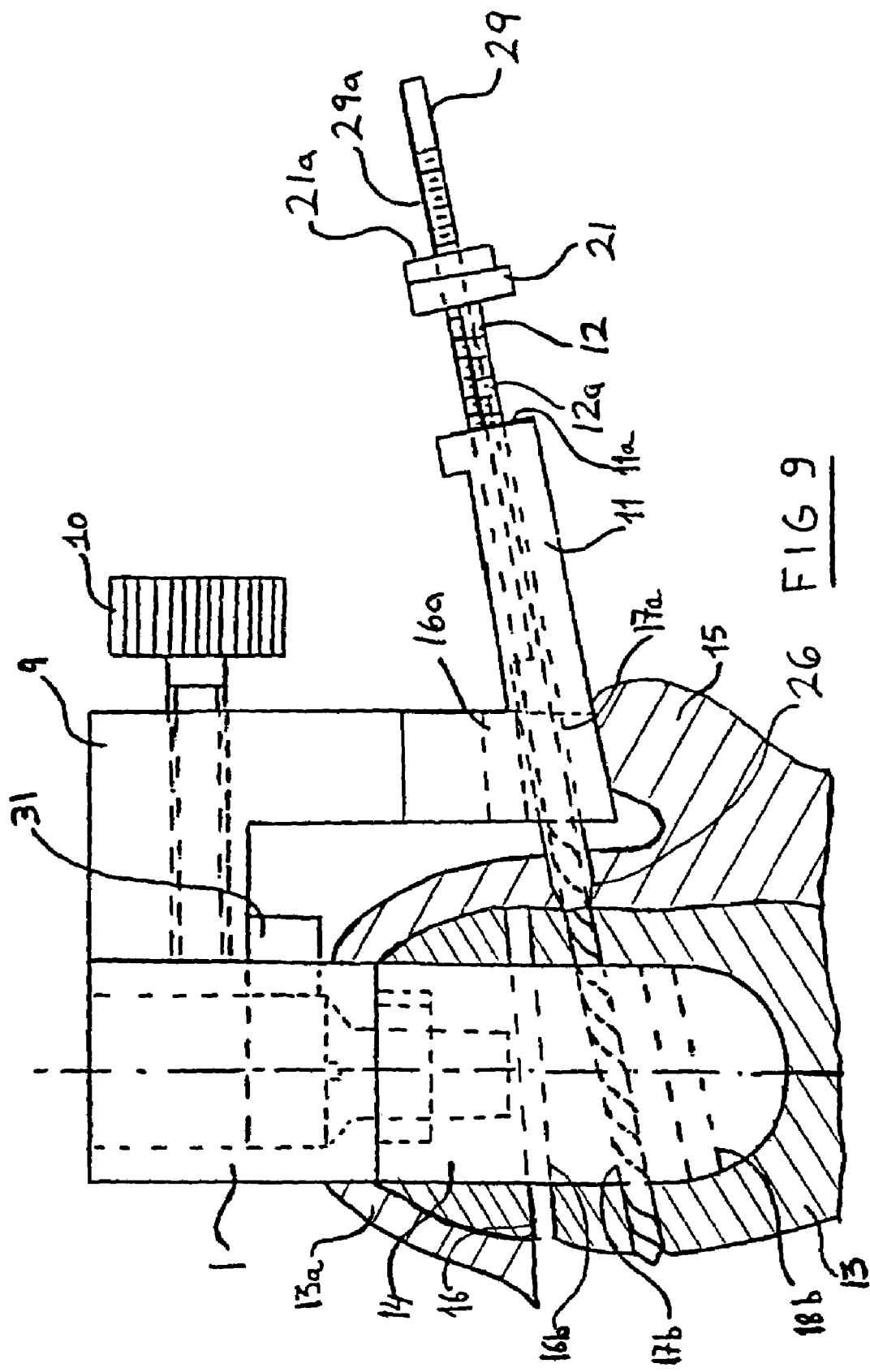

SYSTEM FOR FIXING A DENTAL IMPLANT

CROSS REFERENCE TO RELATED APPLICATIONS

This application is a continuation-in-part of application Ser. No. 10/048,941, filed Feb. 6, 2002 now U.S. Pat. No. 6,824,384 which is the National Stage of International Application No. PCT/FR00/01807, filed Jun. 28, 2000.

FIELD OF THE INVENTION

The present invention concerns equipment for dental surgery, more particularly equipment for inserting dental implants, and chiefly the device specially designed to insert a dental implant before it is secured by pins in the maxillary or mandibulary bone.

BACKGROUND OF THE INVENTION

A device of this type is described in French patent 94 06593.

This application describes an implant that is supported on the upper cortical bone of the maxilla and on the lateral cortical bones by pins, and a particular insertion device.

As for the implant, its body is pierced with bores approximately transverse to its axis, through which one or more cylindrical pins are passed. These pins are inserted into the maxilla through pre-drilled holes in this bone, and pass through the implant via the bores.

These pins, while providing additional supports in the lateral cortical bones, immobilize the implant rotationally around its axis. In other words, the implant cannot pivot on itself and its mounting in the bone is considerably reinforced.

As for the insertion device, it includes a positioning element designed to be attached to the body of the implant in a particularly precise position relative to the bores. This positioning element supports a drilling jig that guides the drill relative to the body of the implant during the drilling of the holes reserved for the pins.

There are known drilling jigs, for example in U.S. Pat. No. 3,981,079. They do not allow for a good adaptation to the anatomical variations of the jaw, or a precise axial insertion of the mounting means.

French patent 94 06593 partially mitigates these drawbacks. It is, however, cumbersome during insertion and during any change in its position, for example when the implant receives several mounting pins at different levels.

BRIEF SUMMARY OF THE INVENTION

One object of the invention is to eliminate these drawbacks.

The subject of the invention is a drilling jig for a dental implant, equipped with a positioning element, particularly an implant having at least one bore designed to receive a pin, said jig having means for locking it into a precise position on such a positioning element, at least one cylindrical pin guiding channel, and means for axially positioning said channel relative to a bony wall receiving an implant pin, characterized in that said axial positioning means include at least one elongated piece or sleeve, of defined length, which contains said channel and is movable along its axis in a jig body that guides it so that it can be brought, at a specially adapted end, in contact with the bony wall.

Preferably, the cylindrical channel also forms a drilling tool guide.

According to a currently preferred embodiment, the positioning element is produced in the form of a tube with a rectilinear axis, open at both ends. It includes an end part having a cross section shaped and sized so as to fit into an axial recess of corresponding cross section, open at the top, provided in the body of the implant. Said end part includes on one of its surfaces a relief, projection or recess designed to cooperate with the relief, recess (or projection) of corresponding shape provided in the wall of the recess of the body of the implant. The latter arrangement plays the role of a "corrector", thus preventing any angular positioning error between the positioning tube and the body of the implant.

Inside its recess, the positioning tube has a conical support surface for the countersunk head of a screw, whose threaded barrel extends outside the tube at the end comprising, for example, a polygonal part. This threaded barrel is designed to be screwed into a corresponding threaded axial blind bore provided in the body of the implant behind said recess of polygonal cross-section.

Again according to a preferred embodiment, the tubular positioning element has a vertical lateral slot. The hole and slot of the positioning element are designed to receive, without play, the corresponding elements of the drilling jig. When the latter is in place inside the positioning element, the practitioner can immobilize it with a mechanical locking mechanism, for example a screw.

The male elements of the drilling jig, i.e. the cylinder and bit, that are inserted into the positioning element are extended at their periphery by a flat part whose profile is, for example, cut in a Z shape.

The upper flat part adjoins the cylinder and the vertical bit that are inserted into the positioning element. The vertical part is pierced in its bottom area with holes, the number of which preferably corresponds to the number of pins that the implant used includes, the axes of which precisely correspond to the axes of these holes. It is possible to slide, into each hole, a guide sleeve of clearly defined length having a thin, conical end that can come into contact with the bone. The surgeon places this sleeve in the hole that corresponds to the pin he is inserting. The body of this guide sleeve, which follows this conical part, is tubular in order to serve as a guide for various instruments, listed below. To facilitate the insertion of these instruments, the continuation of the body of the sleeve is open so that the surgeon can insert them in turn, as needed. The sleeve is long enough for the insertion of these instruments to take place outside the patient's mouth.

In a series of operations as preferably adopted, once the implant has been placed in its cavity bored into the maxillary or mandibulary bone, it can be oriented by pivoting the drilling jig, and hence the implant, relative to the teeth. The choice of its angular orientation is left up to the judgment of the practitioner. When it has been determined that he will proceed with the drilling of the first hole for receiving a pin, he incises the gum by inserting a trocar into the sleeve, then slides the sleeve along the trocar until it contacts the bone. The small wound left by the trocar is minimal and its ulosis occurs very quickly. The drill is inserted into the sleeve in place of the trocar, and it is guided by the sleeve. The sleeve is also used to insert the pin. The latter has at one end a threaded blind hole, into which a pin holder is screwed. The pin and pin holder assembly takes the place of the drill once the drilling of the bone is finished. The pin is impacted using a small surgical mallet to hit the pin holder.

The pin having been inserted, it is released from the pin holder by being unscrewed.

Once the first pin has been set, the sliding sleeve is inserted into a second hole of the drilling jig in order to create a second hole in the bone, unless a second sleeve has been provided.

The obtainment of contact between the sleeve and the jaw bone provides great precision in the drilling of the holes and the insertion of the pins, and as explained below, this allows easy measurement of the length of the holes drilled into the bone.

The fact that the drilling jig is composed of two elements, i.e. the body of the jig and the sliding sleeve, means that the practitioner does not have to remove the jig from the positioning element in order to move it into another position for creating a second hole in the bone, as is the case in the jig described in French patent 94/06593. Only the sleeve is moved, which is much easier and faster. Furthermore, this configuration makes it possible to adjust the jig based on the thickness of the bone, unlike the guide described in U.S. Pat. No. 3,981,079.

In order to allow the practitioner to adapt to his patient's morphology, it is advantageous to provide him with a set of several pins of the same size and shape, but of different lengths. The practitioner would thus be able to choose from these pins the one whose length approximately corresponds to the length of the hole or holes drilled into the bone. The measurement of this length can be determined from graduations on a tool, for example the drilling tool, by referring to a reference mark located on the sliding sleeve.

It may sometimes be necessary to remove one or more pins that have been inserted. Under these conditions, the jig being inserted into the implant holder, the practitioner screws the pin holder back into the pin, then exerts on it a traction supplied by a system generating an extracting force, a lifting screw for example, which is braced between the rear part of the sleeve and the knob that ends the pin holder.

In a preferred embodiment, the jig is configured so that the sleeve can pivot around a point located near its posterior part, so that it can be inserted, as desired, by its anterior part into any of the holes in the jig body. In this case, the passages or bores of the implant have inclined axes that converge at the pivot point. This makes it possible, in particular, to use only one sleeve, which is retracted only a short distance in order to move from one hole to another.

To this end, the flat part of the jig body has a profile, for example cut in a Z shape, whose vertical part, pierced with holes, is extended by a lower part hollowed out by a chute that guides the sleeve and allows it to pivot.

In another embodiment, which makes it possible to have parallel holes, it is necessary either to have one sleeve per hole, or to remove the sleeve from one hole in order to sink it into another hole, keeping in mind that the holes must be long enough to provide, by themselves, a precise guiding of the sleeve.

It is possible to provide means for adjusting the height, i.e. vertically, of the position of the jig on the positioning piece, for example via the insertion or removal of a removable shim. This allows the jig body to have only a limited number of holes, for example just one or two, while making it possible to align the jig with one or more additional bores of the implant by modifying the vertical position of the jig.

BRIEF DESCRIPTION OF THE DRAWINGS

Other advantages and characteristics of the invention will emerge through the reading of the description that follows, written in reference to the attached drawings in which:

FIG. 4 is a view of the sleeve.

FIG. 5 is a view of the pin holder.

FIG. 6 is a view in perspective of a maxillary bone holding an implant secured by 3 pins; it supports the positioning element and the drilling jig.

FIG. 7 gives a view of the pin configured according to the invention.

FIG. 8 is a view of the pin extracting instrument.

FIG. 9 is a front view according to a variant of the device, with a drilling tool present in the sliding sleeve.

DETAILED DESCRIPTION OF THE INVENTION

Figure 1:
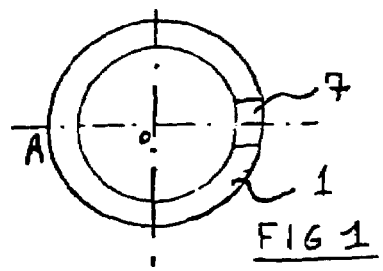
FIG. 1 is a top view of the positioning element.
Figure 2:
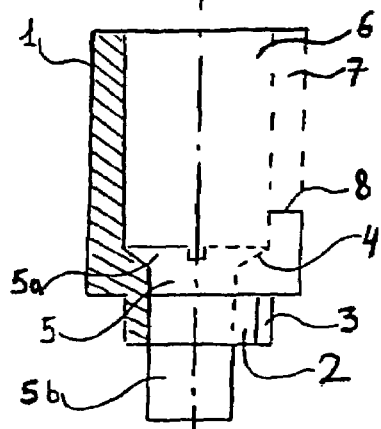
FIG. 2 is a front view and a vertical section in the plane A0 of FIG. 1.

The positioning tube (1) of FIGS. 1 and 2 is of cylindrical shape and circular cross section, and is open at both ends. The tube (1) includes an end part (2) having a regular polygonal cross section, this part being shaped and sized so as to fit into the axial recess of corresponding polygonal cross section provided in the implant body (14).

The end part (2) includes on one of its surfaces a rib (3) designed to fit into the groove of corresponding shape in the implant body (14). This cooperation makes it possible to find the angular position of the piece (1) relative to the body (14), thus providing a corrector that makes it possible to avoid any angular positioning error between the positioning tube (1) and the implant body (14). The internal wall of the positioning tube (1) has a conical support surface (4) for the countersunk head (5a) of a screw (5) whose threaded barrel (5b) extends downward to the outside of the tube (1), at the end comprising the polygonal part (2). This threaded barrel (5b) is designed to be screwed into the threaded axial blind bore provided in the implant body (14) behind the recess of polygonal cross section.

The positioning tube (1), in addition to its vertical axial hole (6), has a vertical slot (7). The hole (6) and slot (7) are designed to receive, without play, the corresponding elements of the drilling jig by sliding in the axial direction of the implant. The latter is inserted as far as the stop (8).

Figure 3:
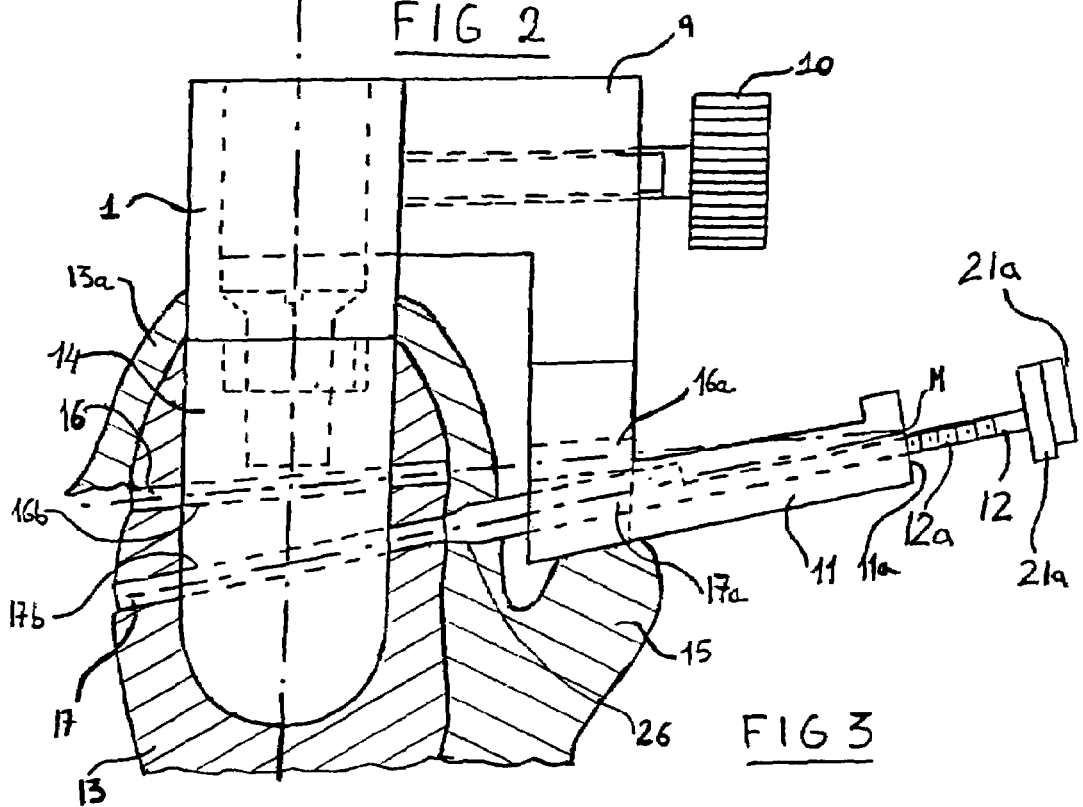
FIG. 3 is a front view of an implant in the process of being set into a maxillary bone represented in section with the gum that covers it. The implant supports the positioning element, which is attached to the drilling jig into which the sliding sleeve has been inserted.

Referring to FIG. 3, we see the positioning tube of FIGS. 1 and 2 screwed into an implant (14) in the process of being set into a maxillary bone (13) covered by the gum (13a). The elements of the positioning tube, the rib (3), the polygonal part (2), and the threaded part (5a) of the screw (5) have been have been inserted into the implant. The positioning tube remains outside the bone. The slot (7) is in the same plane as the transverse holes 16b) and (17b) of the body of the implant (14), and serves to locate the orientation for the surgeon. The part of the drilling jig (9) that follows the cylinder and the vertical bit that enter the positioning element comprises a locking screw (10). This locking screw prevents the risk of a backward movement of the drilling jig inside the positioning element.

It is preferable for the stop (8) to be located high enough in the implant so that the insertion of the drilling jig is not impeded by the gum, if a separation of the latter has not been performed, or by a possible bony relief.

In the bottom of the vertical part (19) of the jig, there are two holes (16a) and (17a) on the axes of the transverse holes 16b) and (17b) of the body of the implant (14); the horizontal part of this jig being the chute (11) which, as may be seen, and given its length, serves as a spreader for the lip (15) or the cheek of the patient in order to facilitate the observation of the site while supporting the sleeve (12), respectively terminated at its two ends by the knob (21) and the cone (26). Before performing the drilling of the holes for the pins (16) and (17), the surgeon can choose the best angle by pivoting the implant, positioning tube and jig assembly around its vertical axis. He can thus estimate the thickness of the bone to be cut through as far as the implant, by maintaining the contact of the cone (26) with the bone (13), an indication being given him by the graduations (12a) on the sleeve, and by referring to a reference mark located on the chute (11), the external edge (11a) for example. It should be noted that the axes of the pins (16) and (17) converge toward the point M at the back of the chute (11). FIG. 4 represents the sleeve (12) in cutaway. It is a metal tube (20) whose end is thin and shaped into a cone (26). This part (20) is followed by a part (22), open along the axis and ending in the knob (21).

FIG. 5 represents the pin holder (23), a simple metal rod that carries the knob (24), and that is screwed into the pin (25).

FIG. 6 represents a partial, schematic view of a maxillary bone (13) into which is inserted the implant (14) onto which is screwed the positioning element (1) into which the drilling jig is inserted. In this configuration, the implant (14) has received 3 pins (16), (17) and (18); the pins (16) and (17) are those of FIG. 3, wherein it was indicated that their axes were convergent at the point M. This provision gives the operator the ability to move the sliding sleeve from one hole to another (16a, 17a or 18a) without having to completely remove it from the jig. The point M constitutes the center of rotation of the sleeve. In the drawing of FIG. 6, the opening of a third hole is visible; it corresponds to the pin (18) whose axis also passes through M. The sleeve (12), open at the top in order to receive the pin holder (23), is placed in the chute (11).

FIG. 7 is enlarged to show, in greater detail, the pin (25), one of whose ends includes a blind threaded hole (26) with an axis identical to that of the pin, so that the pin holder (23) can be screwed into it.

The pin holder and pin assembly is inserted into the sleeve and the pin is impacted into the implant (14). Its passage through the bore can be facilitated by giving the head (24) a few light taps with a surgical mallet. The length of the shaft (27) of the pin holder (23) being equal to that of the sleeve, once the head (24) comes in contact with the end (21) of the sleeve, the practitioner can be sure that the end (28) of the pin has made it all the way to the bone, since the conical end (26) of the sleeve is also there. In case there is a need for this pin to be removed, there is a pin extractor, a small lifting screw (30) for example, represented in FIG. 8, which by pressing against the knob (21) and against the knob (24) separates the two tools and removes the pin from its seat. The shape of the knobs (21) and (24) allows this pin extractor to be inserted easily.

FIG. 9 represents a variant of the device. The implant (14) has a third bore (18b) parallel to the second bore (17b). The drilling jig is vertically adjusted for the creation of the bony hole passing through this bore (18b), by removing the shim (31) from the slot (7) of the positioning element (1). Also represented in this figure is the drilling tool (29) guided by the sleeve (12), the bony hole being finished. The practitioner can precisely estimate the thickness of the bone cut through from the graduations (29a) on the drilling tool, by referring to a reference mark located on the sleeve (12), its external edge (21a) for example.

The guide of the invention is suitable for all types of pins, no matter what their shape.

While this highly precise system has been described above in use with the maxilla, the system is also usable with the mandibula (or mandible). Where the system is used for the mandibula, a different (smaller) size of pin and hence twist drill would be used, since the dense cortical bone of the mandibula would not require as great an engagement area (cylindrical surface) as that of the soft spongious bone of the mandibula. For these two applications, it is anticipated that the diameter measurements of the pins (and drills) would differ to the $300^{th}$ of a millimeter to accommodate the difference in bone density.

While a pin made of CP titanium is satisfactory, this biomaterial will eventually be fully osseo-integrated to the bone. Therefore, it may be extremely difficult to remove using the system described above. In order to make such removal easier, a titanium material which is not so fully osseo-integrated could be considered but such a material might be dangerous to the patient. Therefore, in order to allow for an easier removal of the pins, in accordance with the present invention the pins are made of a polymer material. For example, the pin could be made of a polyaryletherketone polymer. If desired for strength, this polyaryletherketone polymer should additionally contain reinforcing particles, such as carbon or glass fibers, like the PEEK OPTIMA™ material produced by INVIBIO (located in the UK and US).

The invention claimed is:

1. Drilling system for a dental implant, where the dental implant is equipped with a positioning element when located in a bony wall of a mouth of a patient and with a bore, said system comprising:
    an implant pin which is designed to be received through the bony wall and into the bore of the dental implant to secure the dental implant in place;
    a drilling jig including
        a jig body,
        an elongated piece of defined length which is received in said jig body, said elongated piece including a cylindrical pin guiding channel having an axis and a specially adapted end,
        means for locking said jig body into a precise position relative to the positioning element of the dental implant located in the bony wall in the mouth of the patient, and
        means for axially positioning and guiding said elongated piece including said pin guiding channel relative to said jig body and hence relative to the bony wall in the mouth receiving the implant pin, wherein said elongated piece including said pin guiding channel are movable along the axis in said jig body so that said specially adapted end of said elongated piece can be brought in contact with the bony wall, said elongated piece including a stop; and
    a pin holder which is received in said pin guiding channel of said elongated piece to deliver said implant pin into the bore of the dental implant, said pin holder including
        an elongated shaft having, at an anterior end thereof, a means for temporarily fastening to a back end of the implant pin, and
        a stopping member which cooperates with said stop of said elongated piece to provide for an exact axial positioning of the implant pin.

2. Drilling system for a dental implant as claimed in claim 1:
  wherein said implant pin includes at a posterior end having a threaded hole; and
  wherein said means for temporarily fastening of said elongated shaft of said pin holder to said implant pin is a threaded end which is received in said threaded hole of said implant pin.

3. Drilling system for a dental implant as claimed in claim 2, wherein said pin holder is temporarily locked in rotation with the pin.

4. Drilling system for a dental implant as claimed in claim 1, and further including:
  a pin extractor which cooperates with the drilling jig to extract an implant pin received through the bony wall and into the bore of the dental implant therefrom.

5. Drilling system for a dental implant as claimed in claim 4, wherein said pin extractor includes a means for generating an extracting force on said stop and said stopping member.

6. Drilling system for a dental implant as claimed in claim 5, wherein said means for generating an extracting force is a lifting screw.

7. Drilling system for a dental implant as claimed in claim 1, wherein said pin is made of a polymer biocompatible material.

8. Drilling system for a dental implant as claimed in claim 7, wherein said polymer biocompatible material is a polyaryletherketone polymer.

9. Drilling system for a dental implant as claimed in claim 1, wherein said polymer biocompatible material is reinforced by fibers.

10. Drilling system for a dental implant as claimed in claim 9, wherein said fibers are carbon fibers or glass fibers.

11. Drilling system for a dental implant as claimed in claim 10, wherein said polymer biocompatible material is a polyaryletherketone polymer.

12. Drilling system for a dental implant as claimed in claim 1:
  wherein said elongated piece has an insertion end (a) which is opposite to said specially adapted end, (b) which is to be located outside of the mouth, and (c) which is used for the inserting and guiding of various instruments outside of the mouth; and
  wherein said jig body includes an elongated lower part which receives said elongated piece including said pin guiding channel and which additionally serves as a spreader for spreading a lip or cheek of the patient.

* * * * *